United States Patent
Kudlik et al.

(10) Patent No.: US 11,666,281 B2
(45) Date of Patent: Jun. 6, 2023

(54) DETECTION OF HYPERTENSION IN LVAD PATIENTS USING SPEED CHANGE

(71) Applicant: Medtronic, Inc., Minneapolis, MN (US)

(72) Inventors: D'Anne E. Kudlik, Saint Louis Park, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 250 days.

(21) Appl. No.: 16/775,982

(22) Filed: Jan. 29, 2020

(65) Prior Publication Data

US 2020/0275890 A1 Sep. 3, 2020

Related U.S. Application Data

(60) Provisional application No. 62/811,625, filed on Feb. 28, 2019.

(51) Int. Cl.
*A61B 5/00* (2006.01)
*A61B 5/029* (2006.01)
(Continued)

(52) U.S. Cl.
CPC .............. *A61B 5/686* (2013.01); *A61B 5/029* (2013.01); *A61B 5/7282* (2013.01); *A61B 5/746* (2013.01);
(Continued)

(58) Field of Classification Search
CPC ................ A61M 60/148; A61M 60/50; A61M 2205/3334; A61M 2205/3365;
(Continued)

(56) References Cited

U.S. PATENT DOCUMENTS

| | | |
|---|---|---|
| 6,688,861 B2 | 2/2004 | Wampler |
| 7,575,423 B2 | 8/2009 | Wampler |

(Continued)

OTHER PUBLICATIONS

International Search Report and Written Opinion dated May 7, 2020, for corresponding International Application No. PCT/US2020/017587; International Filing Date: Feb. 11, 2020 consisting of 17 pages.

(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

A method of detecting hypertension in a patient having an implantable blood pump, the method includes operating the implantable blood pump at a first pump set speed during a first period of time. A first flow rate minimum during a cardiac cycle of the patient is measured during the first period of time. The first pump set speed is reduced by at least 200 rpm during a second period of time after the first period of time to a second pump set speed, the second period of time being less than the first period of time. A second flow rate minimum is measured during a cardiac cycle during the second period of time. If the second flow rate minimum decreases during the second period of time at the second pump set speed by more than a predetermined amount, an alert is generated indicating a presence of hypertension.

20 Claims, 8 Drawing Sheets

(51) Int. Cl.
*A61M 60/148* (2021.01)
*A61M 60/585* (2021.01)
*A61M 60/531* (2021.01)
*A61M 60/237* (2021.01)
*A61M 60/232* (2021.01)
*A61M 60/178* (2021.01)
*A61M 60/538* (2021.01)
*A61M 60/562* (2021.01)
*A61M 60/523* (2021.01)
*A61M 60/422* (2021.01)

(52) U.S. Cl.
CPC ........ *A61M 60/148* (2021.01); *A61M 60/178* (2021.01); *A61M 60/232* (2021.01); *A61M 60/237* (2021.01); *A61M 60/422* (2021.01); *A61M 60/523* (2021.01); *A61M 60/531* (2021.01); *A61M 60/538* (2021.01); *A61M 60/562* (2021.01); *A61M 60/585* (2021.01); *A61M 2205/3334* (2013.01); *A61M 2205/3365* (2013.01); *A61M 2206/11* (2013.01); *A61M 2206/16* (2013.01)

(58) Field of Classification Search
CPC ........... A61M 2206/11; A61M 2206/16; A61B 5/686; A61B 5/029; A61B 5/7282; A61B 5/746
See application file for complete search history.

(56) References Cited

U.S. PATENT DOCUMENTS

| | | | |
|---|---|---|---|
| 7,963,905 | B2 | 6/2011 | Salmonsen et al. |
| 7,976,271 | B2 | 7/2011 | LaRose et al. |
| 8,007,254 | B2 | 8/2011 | LaRose et al. |
| 8,419,609 | B2 | 4/2013 | Shambaugh, Jr. et al. |
| 9,561,313 | B2 | 2/2017 | Taskin |
| 10,046,098 | B2 | 8/2018 | Poirier |
| 2004/0152944 | A1 | 8/2004 | Medvedev et al. |
| 2005/0159639 | A1 | 7/2005 | Skliar et al. |
| 2007/0282298 | A1 | 12/2007 | Mason |
| 2011/0313238 | A1 | 12/2011 | Reichenbach et al. |
| 2012/0078031 | A1* | 3/2012 | Burke ................. A61M 60/148 600/16 |
| 2013/0046129 | A1* | 2/2013 | Medvedev ............ A61M 60/50 600/16 |
| 2015/0151032 | A1* | 6/2015 | Voskoboynikov .... A61M 60/50 600/17 |
| 2017/0239407 | A1 | 8/2017 | Hayward |
| 2019/0351116 | A1* | 11/2019 | Kudlik ................ A61M 60/546 |

OTHER PUBLICATIONS

Response to Communication Pursuant to Rules 161(1) and 162 EPC dated Oct. 5, 2021, from counterpart European Application No. 20709985.4, filed Mar. 8, 2022, 10 pp.

\* cited by examiner

DETECTION OF HYPERTENSION IN LVAD PATIENTS USING SPEED CHANGE

CROSS-REFERENCE TO RELATED APPLICATION

This application claims the benefit of U.S. Application Ser. No. 62/811,625, filed Feb. 28, 2019.

FIELD

The present technology is generally related to ventricular assist devices and detection of hypertension in patients.

BACKGROUND

Patients with ventricular assist devices, VADs, must routinely have their blood pressure monitored to maximize the benefits received from such devices and reduce the risk of adverse events associated with hypertension. Unlike some adverse events, such as suction in an implantable blood pump, hypertension cannot be resolved by reducing the speed of the pump. However, under normal pump operating conditions, it is difficult to distinguish a suction condition, which can be resolved by reducing pump speed, versus hypertension which cannot.

SUMMARY

The techniques of this disclosure generally relate to a method of detecting hypertension in a patient having a ventricular assist device, and in particular an implantable blood pump. The method includes operating the implantable blood pump at a first pump set speed during a first period of time. At least one from the group consisting of a first flow rate pulsatility and a first current pulsatility is measured during the first period of time. The first pump set speed is reduced during a second period of time after the first period of time to a second pump set speed. At least one from the group consisting of a second flow rate pulsatility and a second current pulsatility is measured during the second period of time. If the at least one from the group consisting of the second flow rate pulsatility and the second current pulsatility increases during the second period of time at the second pump set speed compared to the at least one from the group consisting of the first flow rate pulsatility and the first current pulsatility at the first pump set speed during the first period of time, an alert is generated indicating a presence of hypertension.

In another aspect, if the alert is generated indicating the presence of hypertension, the method further includes identifying the at least one from the group consisting of the first flow rate pulsatility and the first current pulsatility at the first pump set speed during the first period of time as a non-suction waveform.

In another aspect, the second pump set speed is at least 200 rpm less that the first pump set speed.

In another aspect, the second period of time is less than the first period of time.

In another aspect, during continuous operation of the implantable blood pump, the first period of time and the second period of time are consecutive.

In another aspect, the first period of time and the second period of time are periodic at predetermined intervals.

In another aspect, the implantable blood pump is a centrifugal flow blood pump.

In another aspect, the implantable blood pump is an axial flow blood pump.

In another aspect, the first flow rate pulsatility and the second flow rate pulsatility are measured.

In another aspect, the first current pulsatility and the second current pulsatility are measured.

In another aspect, the first flow rate pulsatility and the second flow rate pulsatility are determined from at least one from the group consisting of a mean and a median from a plurality of cardiac cycles during the respective one of the first period of time and the second period of time.

In another aspect, the first current pulsatility and the second current pulsatility are determined from at least one from the group consisting of a mean and median from a plurality of cardiac cycles during the respective one of the first period of time and the second period of time.

In one aspect, a system for detecting hypertension in a patient having a ventricular assist device, the ventricular assist device including an implantable blood pump, includes a controller in communication with the implantable blood pump, the controller having a processor having processing circuity, the processing circuitry being configured to operate the implantable blood pump at a first pump set speed during a first period of time. At least one from the group consisting of a first flow rate minimum and a first current minimum is measured during a first period of time. The first pump set speed is reduced during a second period of time after the first period of time to a second pump set speed. At least one from the group consisting of a second flow rate minimum and a second current minimum is measured during the second period of time. If the at least one from the group consisting of the second flow rate minimum and the second current minimum decreases during the second period of time at the second pump set speed more than a predetermined amount, the controller is configured to at least one from the group consisting of increase the second pump set speed to the first pump set speed and generate an alert indicating a presence of hypertension.

In another aspect, if the alert is generated indicating the presence of hypertension, the processing circuity is further configured to identify the at least one from the group consisting of the first flow rate minimum and the first current minimum at the first pump set speed during the first period of time as a non-suction waveform.

In another aspect, the second pump set speed is at least 200 rpm less that the first pump set speed.

In another aspect, the second period of time is less than the first period of time.

In another aspect, during continuous operation of the implantable blood pump, the first period of time and the second period of time are consecutive.

In another aspect, the first period of time and the second period of time are periodic at predetermined intervals.

In another aspect, the implantable blood pump is a centrifugal flow blood pump.

In another aspect, the implantable blood pump is an axial flow blood pump.

In another aspect, the first flow rate minimum and the second flow rate minimum are determined from at least one from the group consisting of a mean and a median from a plurality of cardiac cycles during the respective one of the first period of time and the second period of time.

In another aspect, the first current minimum and the second current minimum are determined from at least one from the group consisting of a mean and a median from a plurality of cardiac cycles during the respective one of the first period of time and the second period of time.

In one aspect, a method of detecting hypertension in a patient having a ventricular assist device, the ventricular assist device including an implantable blood pump, the method includes operating the implantable blood pump at a first pump set speed during a first period of time. A first flow rate minimum during a cardiac cycle of the patient is measured during the first period of time. The first pump set speed is reduced by at least 200 rpm during a second period of time after the first period of time to a second pump set speed, the second period of time being less than the first period of time. A second flow rate minimum is measured during a cardiac cycle during the second period of time. If the second flow rate minimum decreases during the second period of time at the second pump set speed by more than a predetermined amount, an alert is generated indicating a presence of hypertension.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
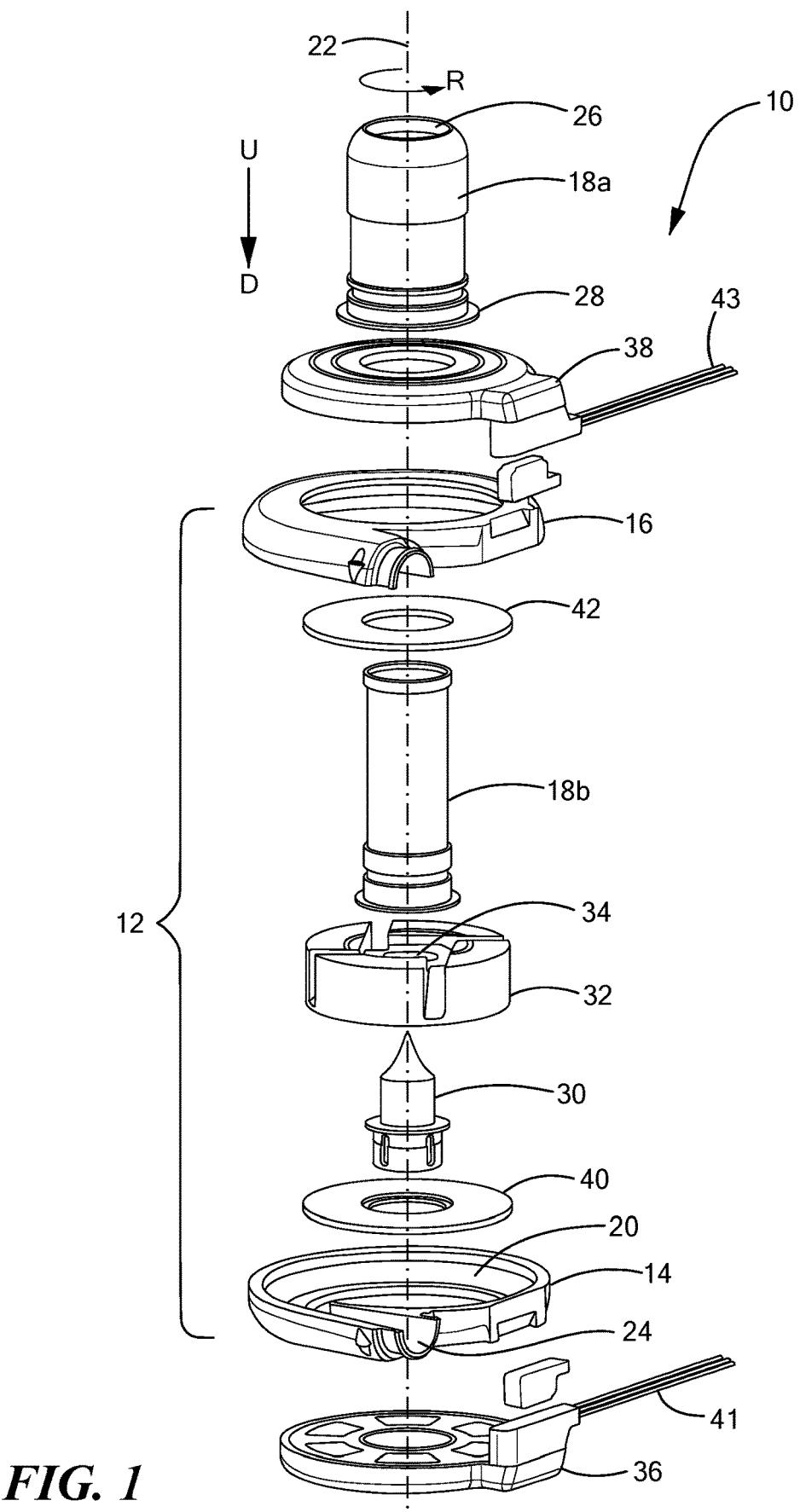
FIG. 1 is an exploded view of an implantable blood pump constructed in accordance with the principles of the present application.

Referring now to the drawings in which like reference designators refer to like elements there is shown in FIG. 1 an exemplary ventricular assist device, and in particular, an implantable blood pump constructed in accordance with the principles of the present application and designated generally "10." The blood pump 10, according to one embodiment of the disclosure, includes a static structure or housing 12 which houses the components of the blood pump 10. In one configuration, the housing 12 includes a lower housing or first portion 14, an upper housing or second portion 16, and an inlet element 18 or inflow cannula 18 which includes an outer tube 18a and an inner tube 18b. The first portion 14 and the second portion 16 cooperatively define a volute shaped chamber 20 having a major longitudinal axis 22 extending through the first portion 14 and the inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls. The inflow cannula 18 is generally cylindrical and extends generally from the first portion 14 along the axis 22. The inflow cannula 18 has an upstream end or proximal end 26 remote from second portion 16 and a downstream end or distal end 28 proximate the chamber 20.

The parts of the housing 12 mentioned above are fixedly connected to one another so that the housing 12 as a whole defines a continuous enclosed flow path. The flow path extends from the upstream end 26 at the upstream end of the flow path to the outlet 24 at the downstream end of the flow path. The upstream and downstream directions along the flow path are indicated in by the arrows U and D, respectively. A post 30 is mounted to the first portion 14 along the axis 22. A generally disc shaped ferromagnetic rotor 32 with a central hole 34 is mounted within the chamber 20 for rotation about the axis 22. The rotor 32 includes a permanent magnet and flow channels for transferring blood from adjacent the center of the rotor 32 to the periphery of the rotor 32. In the assembled condition, the post 30 is received in the central hole of the rotor 32.

A first stator or motor 36 having a plurality of coils may be disposed within the first portion 14 downstream from the rotor 32. The first stator 36 may be axially aligned with the rotor along the axis 22 such that when a current is applied to the coils in the first stator 36, the electromagnetic forces generated by the first stator 36 rotate the rotor 32 and pump blood. A second stator or motor 38 may be disposed within the second portion 16 upstream from the rotor 32. The second stator 38 may be configured to operate in conjunction with or independently of the first stator 36 to rotate the rotor 32.

Electrical connectors 41 and 43 (FIG. 1) are provided on the first portion 14 and the second portion 16, respectively, for connecting the coils to a source of power, such as a controller (not shown). The controller is arranged to apply power to the coils of the pump to create a rotating magnetic field which spins the rotor 32 around the axis 22 in a predetermined first direction of rotation, such as the direction R indicated by the arrow which is counterclockwise as seen from the upstream end of the inflow cannula 18. In other configurations of the blood pump 10, the first direction may be clockwise. Rotation of the rotor 32 impels blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with the surfaces of the elements of the first portion 14 and the second portion 16 during operation.

A first non-ferromagnetic disk 40 may be disposed within the first portion 14 upstream from the rotor 32 between the first stator 36 and the rotor 32 and a second non-ferromagnetic disk 42 may be disposed downstream from the rotor 32 within the second portion 16 between the second stator 38 and the rotor 32. The rotor 32 is configured to rotate between the first disk 40 and the second disk 42 without contacting either disk. The general arrangement of the components described above may be similar to the blood pump 10 used in the MCSD sold under the designation HVAD® by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Other implantable blood pumps 10 contemplated by this disclosure are those disclosed in U.S. Pat. Nos. 8,007,254 and 9,561,313, incorporated by reference herein, and are axial flow blood pumps The MVAD™ pump is currently not for sale.

Figure 2:
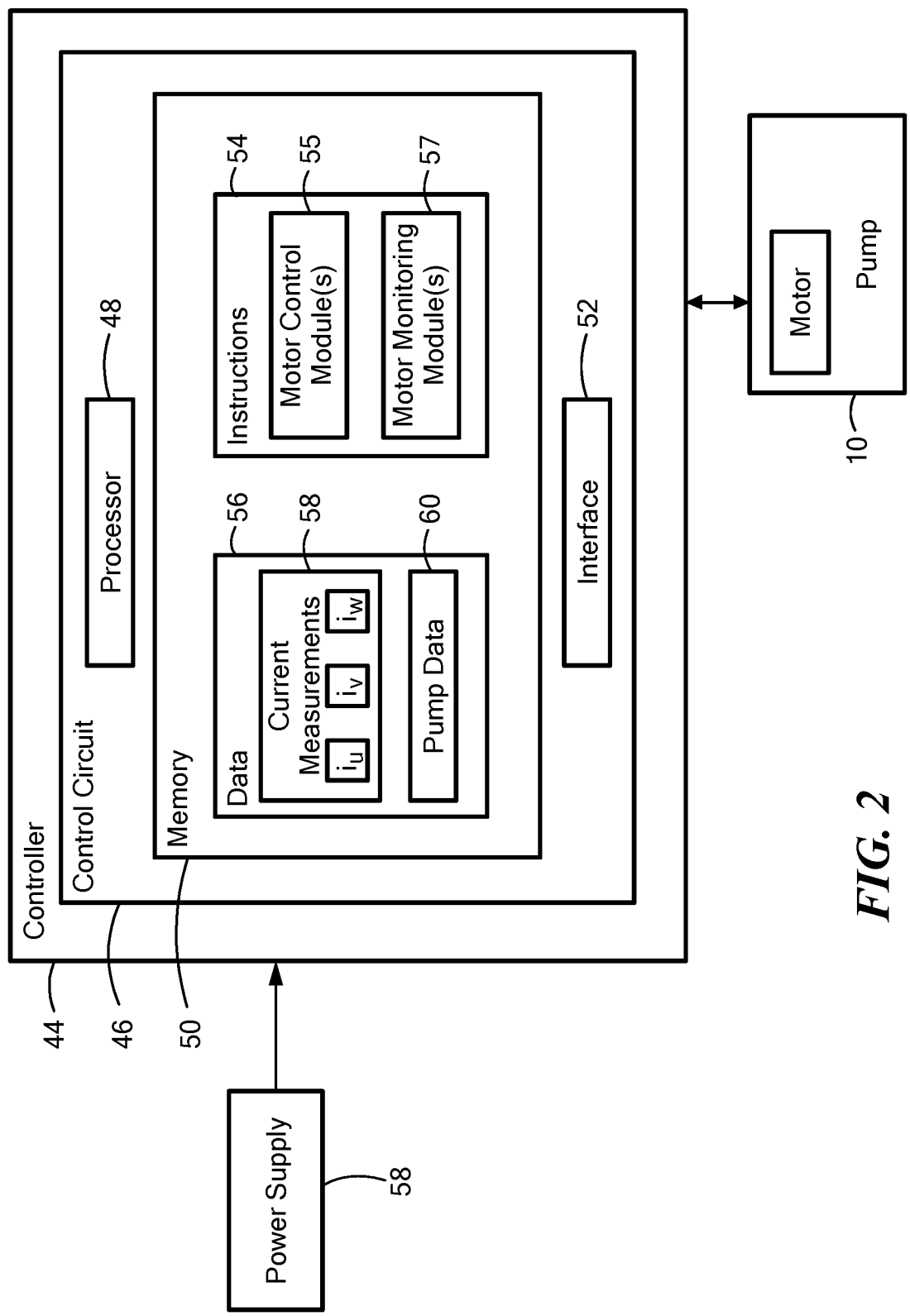
FIG. 2 is a block diagram illustrating the various components of a controller of the present application.

Referring now to FIG. 2, implantable blood pump 10 may be in communication with a controller 44 having a control circuit 46 having control circuitry for monitoring and controlling startup and subsequent operation of one or more motors of the implanted blood pump 10. The controller 44 may also include a processor 48 having processing circuitry, a memory 50, and an interface 52. The memory 50 stores information accessible by the processor 48 and processing circuitry, including instructions 54, for example, motor control modules 55 and motor monitoring modules 57 executable by the processor 20 and/or data 56, which may include by its not limited to, current 58 supplied to the one or more motors in one or more phases motors and pump data 60, which may include flow rate date, that may be retrieved, manipulated, and/or stored by the processor 20. The controller 44 may be in communication with a power supply 58 which may be external to the patient, for example, a battery 62.

Figure 3:
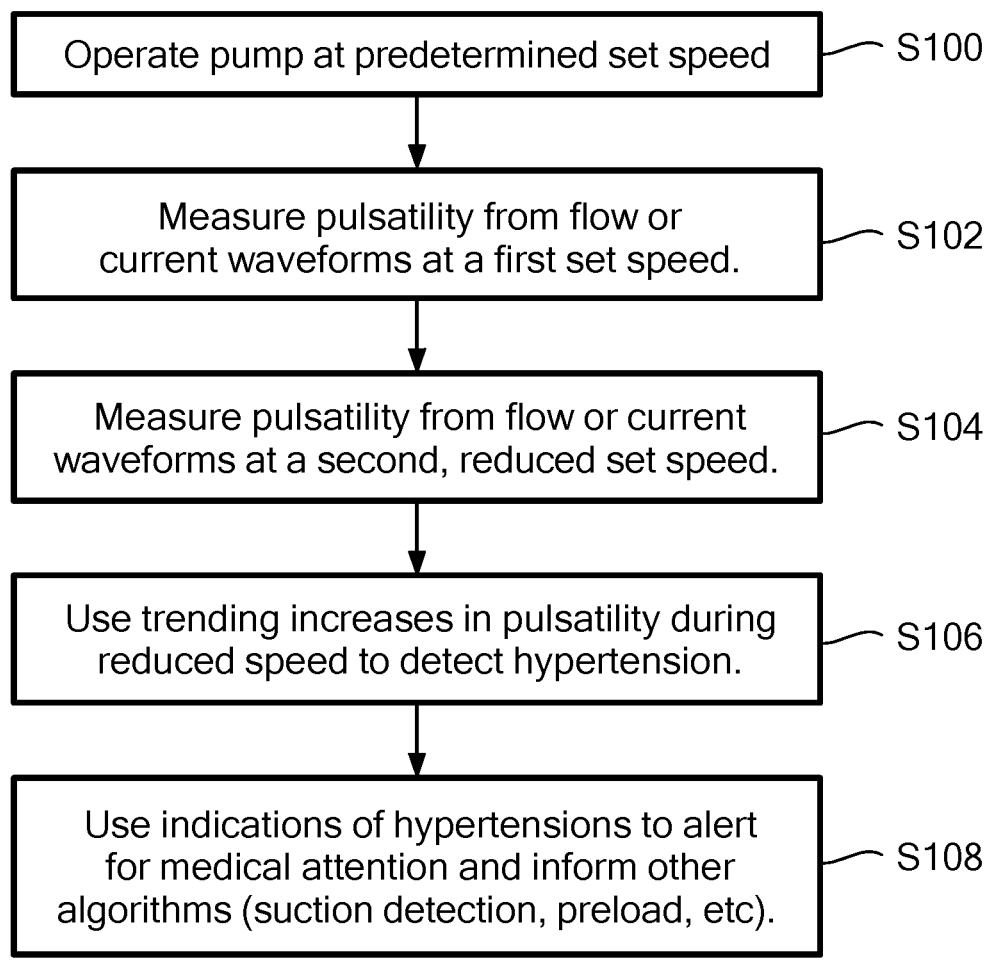
FIG. 3 is a flow chart illustrating a method of detecting hypertension in a patient having and implantable blood pump in accordance with one aspect of the present application.
Figure 4:
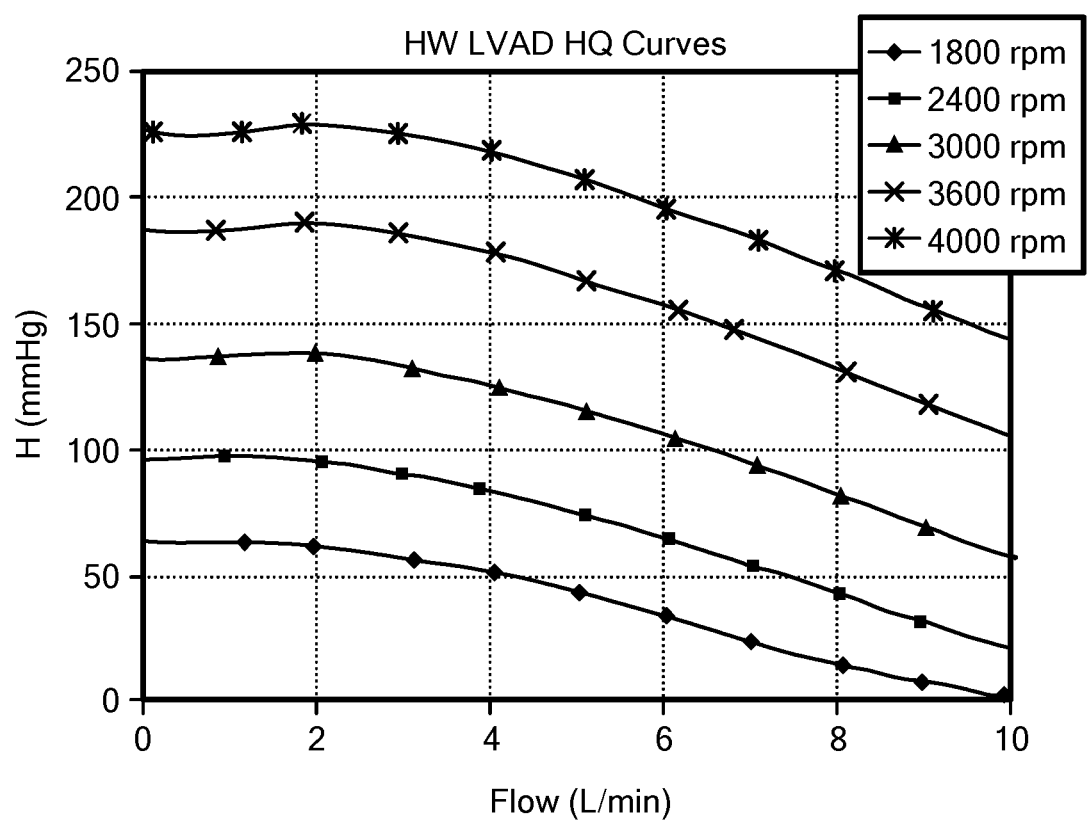
FIG. 4 is a graph showing the HQ curves for an exemplary ventricular assist device at various predetermined pump set speeds.

Referring now to FIG. 3, during operating of the pump 10, the controller 44 may operate the implantable blood pump 10 at a first pump set speed $S_1$ of the impeller 32 during a first period of time (Step S100). The first pump set speed $S_1$ may range between, for example, 1800 rpm and 4000 rpm, and may be a function of the particular pump, whether a centrifugal flow pump or an axial flow pump. For example, as shown in FIG. 4 for each first pump set speed, $S_1$, the pump 10 exhibits a particular HQ curve that generally shows that during normal use fluid flow out through the pump increases as the pressure head decreases regardless of the set speed. Fluid flow is also a function of a patient's cardiac cycle, where during diastole the pressure head is higher and fluid flow decreases out through the pump 10 and during systole the pressure head decreases and fluid flow increases out through the pump 10. During normal operation at the first pump set speed, $S_1$, the current waveform and the flow rate waveform may be measured in real time and monitored by the controller 44 (Step S102). As used herein, "hypertension" or "hypertensive" refers to hypertension or operation in the flat region of the HQ curve.

Figure 5:
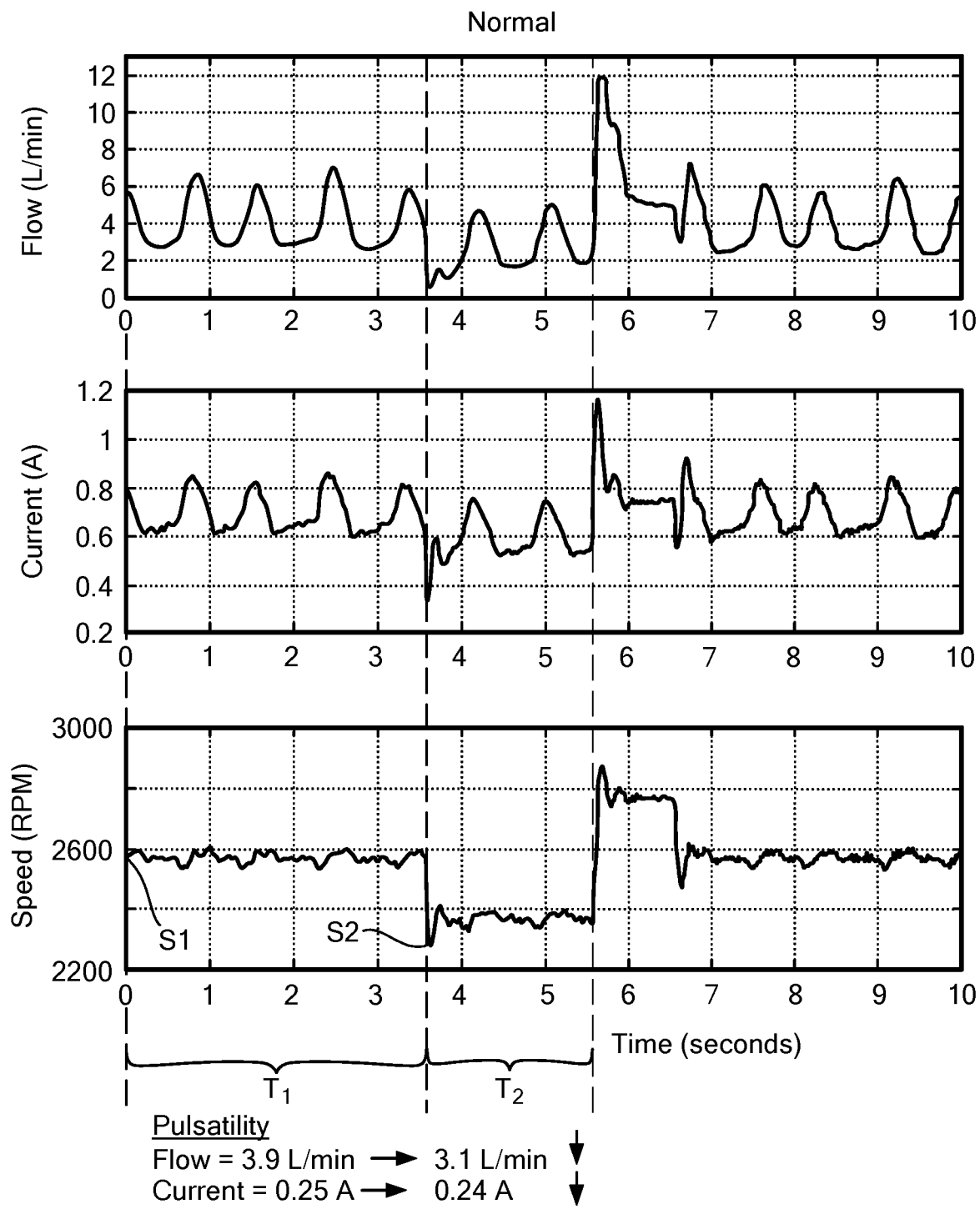
FIG. 5 is graph showing an exemplary flow rate and current waveform at first and second predetermined pump set speeds in a patient with normal blood pressure and the corresponding pulsatility.
Figure 6:
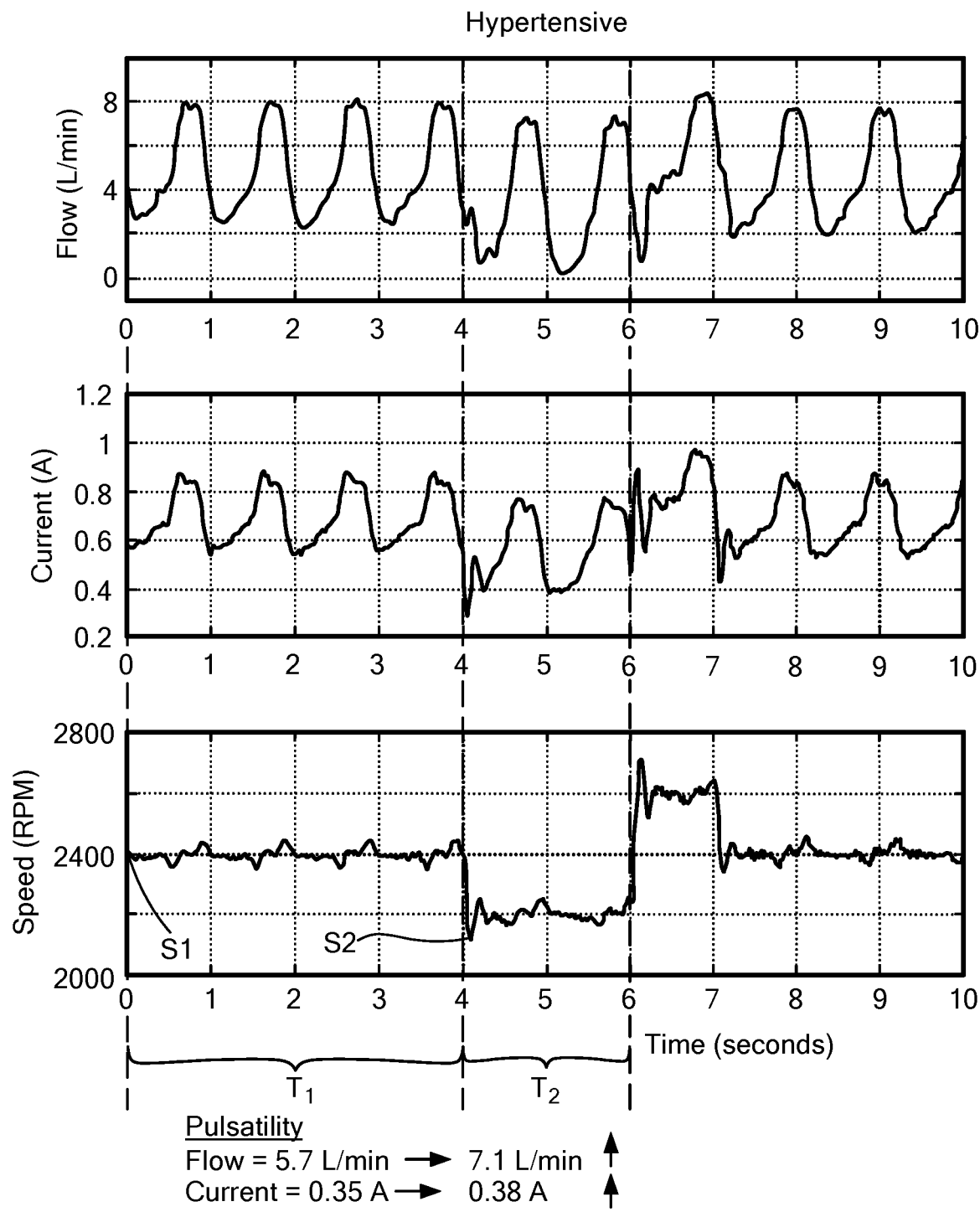
FIG. 6 is graph showing an exemplary flow rate and current waveform at first and second predetermined pump set speeds in a patient with normal hypertension and the corresponding pulsatility.

In one configuration, as shown in FIG. 5, a patient with a normal blood pressure exhibits a first flow pulsatility of about 3.9 L/min, and a first current pulsatility of around 0.25 A, during a first time period $T_1$ at the first pump set speed, S1 2600 RPM. In one configuration, a patient with hypertension, as shown in FIG. 6, exhibits a first flow pulsatility of about 5.7 L/min, and a first current pulsatility of about 0.35 A, during a first time period $T_1$ at the first pump set speed, S1 2400 RPM. Thus, a hypertensive patient has greater pulsatility of flow rate and current than a patient with normal blood pressure. For example, as shown in both FIGS. 5 and 6, the controller 44 may reduce the speed of the impeller 32 by a predetermined amount to a second pump set speed $S_2$ of the impeller 32 during a second period of time $T_2$ (Step S104). For example, as shown in FIGS. 5 and 6, the first pump set speed, $S_1$ is reduced by 200 RPM to the second pump set speeds $S_2$ of 2200 RPM and 2400 RPM, respectively. The second period of time $T_2$ may be the less than, the same, or longer than the first period of time $T_1$. Optionally, the time periods $T_1$, where the set speed is normal, and $T_2$, where the set speed is reduced, may be run periodically and/or continually as part of normal operation of the blood pump or as part of a normal impeller 32 wash cycle, in which the speed of the impeller 32 is decreased then increased to prevent thrombus formation on the impeller 32.

During the second period of time $T_2$ at the reduced set speed $S_2$, the flow rate and the current are measured (Step S106). If a second flow rate pulsatility or a second current pulsatility increases during the second period of time, $T_2$, at the second pump set speed, $S_2$, compared to respective one of the first flow rate pulsatility or the first current pulsatility at the first pump set speed during $S_1$, the first period of time, $T_1$, the controller 44 may determine that the patient is exhibiting hypertension (Step 108). For example, as shown in FIG. 5, the second flow rate pulsatility during the second period of time, $T_2$ at the second pump set speed, $S_2$, decreases from 3.9 L/min to 3.1 L/min and the second current pulsatility during the second period of time, T2 at the second pump set speed, S2, decreases from 0.25 A to 0.24 A. This decrease in pulsatility of current and/or flow rate is indicative of a patient with normal blood pressure. However, as shown in FIG. 6, the second flow rate pulsatility during the second period of time, $T_2$ at the second pump set speed, $S_2$, increases from an already higher than normal 5.7 L/min to 7.1 L/min, and the second current pulsatility during the second period of time, T2 at the second pump set speed, S2, increases from an already higher than normal 0.35 A to 0.38 A. This increase in pulsatility of current and/or flow rate is indicative of hypertension, which can be determined by the controller 44. The measured flow rate pulsatility or current pulsatility may further be based on a measured mean or median of the respective pulsatility over $T_1$ and/or $T_2$.

In another method of detection hypertension, during operation of the blood pump 10, the flow rate or current minimum during $T_1$ at the first pump set speed, $S_1$, may be measured. The flow rate or current minimum may be measured during a single cardiac cycle during $T_1$, may be the mean of the minimum flow rates or currents detected from each of a number of cardiac cycles during $T_1$, or the median of the minimum flow rate or current detected from each of a number of cardiac cycles during $T_1$. The controller 44 may then reduce the impeller 32 speed to $S_2$ during $T_2$ and the flow rate or current minimum is then measured during $T_2$, which may be measured during a single cardiac cycle during $T_2$, may be the mean of the minimum flow rates or currents detected from each of a number of cardiac cycles during $T_2$, or the median of the minimum flow rates or currents detected from each of a number of cardiac cycles during $T_2$, depending on how the minimum flow rate or current minimum is measured during $T_1$. If the measured minimum flow rate or current minimum decreases during $T_2$ at $S_2$ by more than a predetermined amount, then the controller 44 may indicate the presence of hypertension by generating an alert as described above and/or the controller may direct the set speed of the impeller 32 to either stay at $S_2$ or return to a set speed equal to or greater than $S_1$. The predetermined decrease in current may be based on empirical values of patients that have a normal blood pressure. For example, as shown in FIG. 5, the measured flow or current minimum during $T_2$ at $S_2$ in a patient with normal blood pressure decreases by less than the measured flow or current minimum during $T_2$ at $S_2$ in a patient with hypertension. For example, in FIG. 5, the flow rate minimum at its lowest during $T_2$ at $S_2$ is about 1 L/min whereas in FIG. 6, it approaches 0 L/min in patient with hypertension.

Figure 7:
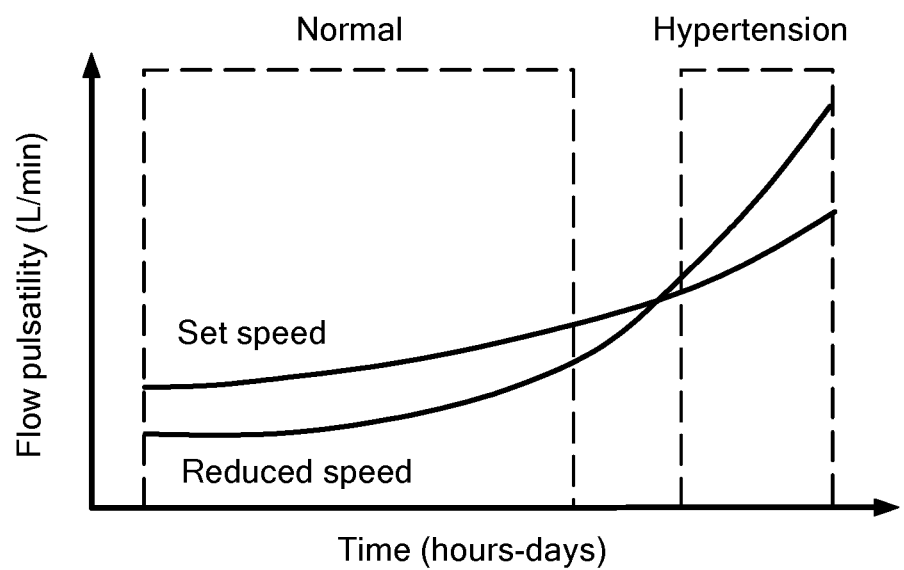
FIG. 7 is a graph showing that the relationship between flow rate pulsatility at a first set speed and a reduced speed can identify the development of hypertension over a long period of time.
Figure 8:
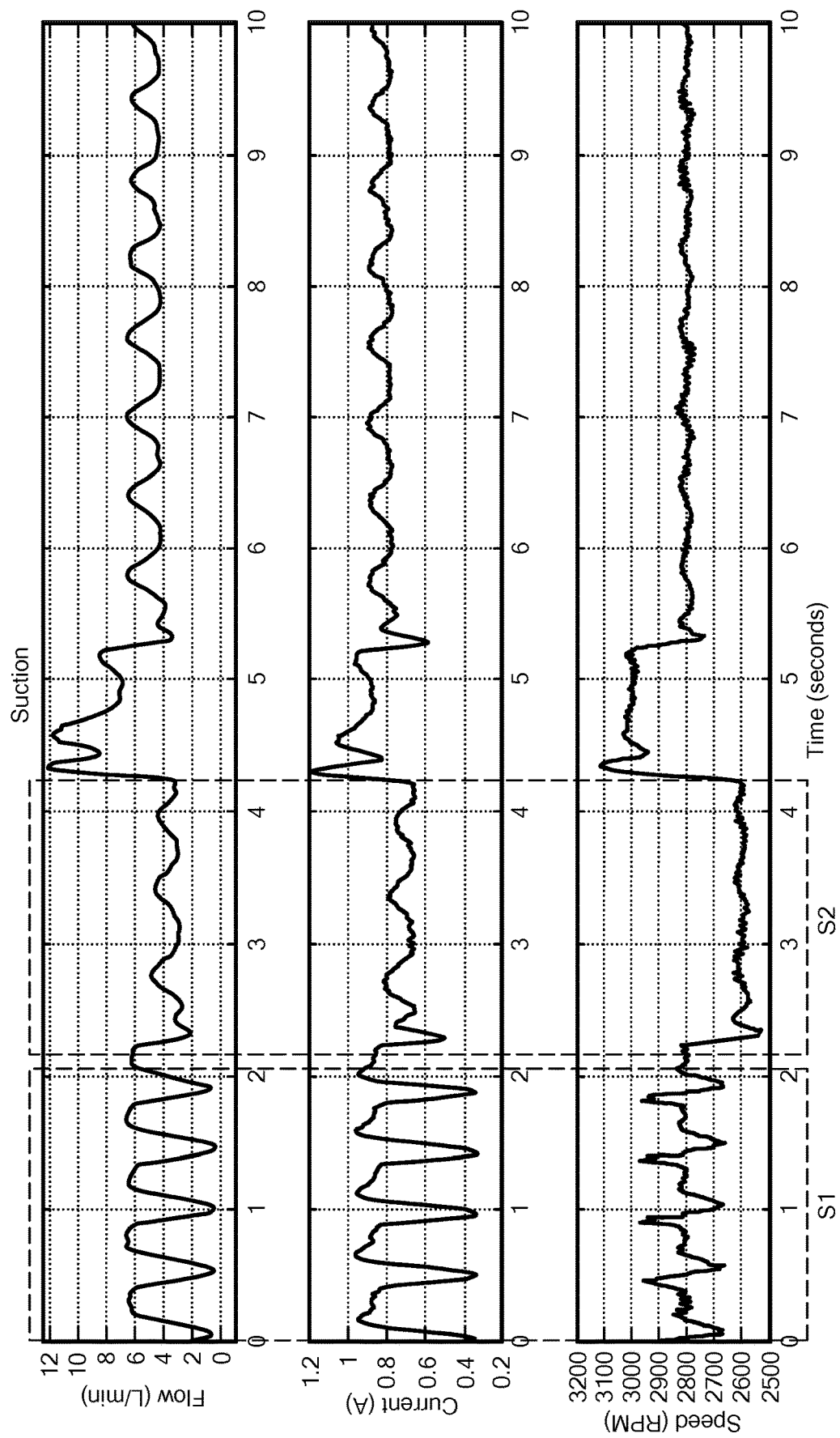
FIG. 8 is a graph showing resolution of a suction condition when speed of the impeller is reduced.

Referring now to FIGS. 7 and 8, if a suction condition is present, the increased pulsatility of flow and/or current and/or the decreased the minimum of flow and/or current is measured by the controller 44, and reducing the set speed of the impeller 32 should resolve or not exacerbate the condition. For example, as shown in FIG. 8, when the impeller 32 speed is reduced the measured flow rate pulsatility and current pulsatility reduces. However, if pulsatility increases or the minimum of flow or current decreases during $T_2$ with a reduced set speed, the controller 44 may flag the log file and/or in real time generate an alert, whether visual, tactile, or audio indicating the presence of hypertension, and not a suction related current or flow rate waveform, and inform other suction related algorithms that hypertension is present. This determination may therefore result in modification of the suction detection criteria thereafter.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of detecting hypertension in a patient having a ventricular assist device, the ventricular assist device including an implantable blood pump, the method comprising:
    operating the implantable blood pump at a first pump set speed during a first period of time;
    measuring a first pulsatility during the first period of time, the first pulsatility corresponding to at least one of a first flow rate pulsatility or a first current pulsatility;
    reducing the first pump set speed during a second period of time after the first period of time to a second pump set speed;
    measuring a second pulsatility during the second period of time, the second pulsatility corresponding to at least one of a second flow rate pulsatility or a second current pulsatility; and
    in response to the second pulsatility increasing during the second period of time compared to the first pulsatility during the first period of time, identifying that the patient has exhibited hypertension.

2. The method of claim 1, further comprising:
    in response to the second pulsatility increasing during the second period of time compared to the first pulsatility during the first period of time, generating an alert identifying that the patient has exhibited hypertension.

3. The method of claim 1, wherein the second pump set speed is at least 200 rpm less than the first pump set speed.

4. The method of claim 1, wherein the second period of time is less than the first period of time.

5. The method of claim 1, wherein during continuous operation of the implantable blood pump, the first period of time and the second period of time are consecutive.

6. The method of claim 5, wherein the first period of time and the second period of time are periodic at predetermined intervals.

7. The method of claim 1, wherein the implantable blood pump is a centrifugal flow blood pump.

8. The method of claim 1, wherein the implantable blood pump is an axial flow blood pump.

9. The method of claim 1, wherein the first pulsatility corresponds to the first flow rate pulsatility and the second pulsatility corresponds to the second flow rate pulsatility.

10. The method of claim 1, wherein the first pulsatility corresponds to the first current pulsatility and the second pulsatility corresponds to the second current pulsatility.

11. A system for detecting hypertension in a patient having a ventricular assist device, the ventricular assist device including an implantable blood pump, the system comprising:
    memory; and
    a controller coupled to the memory, comprising circuitry, and configured to:
        operate the implantable blood pump at a first pump set speed during a first period of time;
        measure a first pulsatility during the first period of time, the first pulsatility corresponding to at least one of a first flow rate pulsatility or a first current pulsatility;
        reduce the first pump set speed during a second period of time after the first period of time to a second pump set speed;

measure a second pulsatility during the second time period, the second pulsatility corresponding to at least one of a second flow rate pulsatility or a second current pulsatility; and in response to the second pulsatility increasing during the second period of time at the second pump set speed compared to the first pulsatility at the first pump set speed during the first period of time, identify that the patient is exhibiting hypertension.

12. The system of claim 11, wherein the controller is further configured to:

generate an alert identifying that the patient has exhibited hypertension in response to the second pulsatility increasing during the second period of time at the second pump set speed compared to the first pulsatility at the first pump set speed during the first period of time.

13. The system of claim 11, wherein the second pump set speed is at least 200 rpm less than the first pump set speed.

14. The system of claim 11, wherein the second period of time is less than the first period of time.

15. The system of claim 11, wherein during continuous operation of the implantable blood pump, the first period of time and the second period of time are consecutive.

16. The system of claim 15, wherein the first period of time and the second period of time are periodic at predetermined intervals.

17. The system of claim 11, wherein the implantable blood pump is a centrifugal flow blood pump.

18. The system of claim 11, wherein the implantable blood pump is an axial flow blood pump.

19. The system of claim 11, wherein the first pulsatility corresponds to the first flow rate pulsatility and the second pulsatility corresponds to the second flow rate pulsatility.

20. The system of claim 11, wherein the first pulsatility corresponds to the first current pulsatility and the second pulsatility corresponds to the second current pulsatility.

* * * * *